United States Patent
Bob

(10) Patent No.: US 12,251,154 B2
(45) Date of Patent: Mar. 18, 2025

(54) SURGICAL INSTRUMENT

(71) Applicant: Erbe Elektromedizin GmbH, Tuebingen (DE)

(72) Inventor: Felix Bob, Rottenburg (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 596 days.

(21) Appl. No.: 17/224,385

(22) Filed: Apr. 7, 2021

(65) Prior Publication Data

US 2021/0322087 A1 Oct. 21, 2021

(30) Foreign Application Priority Data

Apr. 15, 2020 (EP) .................................. 20169631

(51) Int. Cl.
*A61B 18/14* (2006.01)

(52) U.S. Cl.
CPC ...... *A61B 18/1442* (2013.01); *A61B 18/1445* (2013.01); *A61B 2018/1455* (2013.01)

(58) Field of Classification Search
CPC .............. A61B 17/2816; A61B 17/285; A61B 18/1442; A61B 18/1445; A61B 2017/2845; A61B 2018/00196; A61B 2018/00202; A61B 2018/1455
USPC ..................................................... 606/51–52
See application file for complete search history.

(56) References Cited

U.S. PATENT DOCUMENTS

| | | | |
|---|---|---|---|
| 9,445,825 B2 | 9/2016 | Belaney et al. | |
| 10,045,811 B2 | 8/2018 | Sharp et al. | |
| 2012/0209263 A1 | 8/2012 | Sharp et al. | |
| 2013/0041402 A1* | 2/2013 | Chojin | A61B 17/285 606/206 |
| 2013/0296843 A1 | 11/2013 | Boudreaux et al. | |
| 2016/0331396 A1 | 11/2016 | Schweitzer et al. | |
| 2017/0209205 A1 | 7/2017 | Cho et al. | |
| 2017/0296195 A1 | 10/2017 | Pleil et al. | |
| 2019/0357964 A1 | 11/2019 | Boudreaux | |
| 2020/0138462 A1* | 5/2020 | Vogtherr | A61B 17/3201 |

FOREIGN PATENT DOCUMENTS

| | | |
|---|---|---|
| CN | 107072670 A | 8/2017 |
| EP | 2 436 327 A1 | 4/2012 |
| JP | H0280024 A | 3/1990 |
| JP | 2017502814 A | 1/2017 |
| KR | 20120136584 A | 12/2012 |
| KR | 10-1298237 B1 | 8/2013 |
| RU | 2096997 C1 | 11/1997 |

* cited by examiner

Primary Examiner — Khadijeh A Vahdat
(74) *Attorney, Agent, or Firm* — Blank Rome LLP

(57) ABSTRACT

An operation device for operating a tool of a surgical instrument. The operation device has an operation element that is pivotably supported between an initial position and a working position. The operation element is movably coupled with the tool by means of a coupling device comprising a coupling link or consisting of a coupling link. The coupling link is elastically deformable and effectuates a resetting torque due to the elastic deformation in case the operation element is deflected out of the initial position, wherein the resetting torque urges the operation element back in the initial position.

12 Claims, 6 Drawing Sheets

SURGICAL INSTRUMENT

CROSS-REFERENCE TO RELATED APPLICATION

This application claims priority to European Application No. 20169631.7, filed Apr. 15, 2020, the entirety of which is incorporated by reference herein.

BACKGROUND

Embodiments of the invention include a surgical instrument, e.g. an electrosurgical instrument. The surgical instrument can have two jaws that are pivotably supported at one another. On the surgical instrument a tool, e.g. a knife, is provided that is movably supported in a longitudinal direction in a guided manner. The knife can be supported in a knife channel. The knife can be moved in longitudinal direction by means of an operation element in order to cut biological tissue that is clamped between the jaws.

EP 2 436 327 A1 describes a surgical forceps with two jaws that are pivotably supported at one another and a knife that is guided in a longitudinal direction. The knife can be moved in longitudinal direction by means of a pivotably supported operation element. A helical spring is provided to bias the operation element in an initial position, wherein the helical spring is tensioned and creates a resetting torque in direction toward the initial position, if the operation element is deflected from its initial position.

US 2017/0209205 A1 describes a bipolar surgical forceps with two jaws that are pivotably supported at one another and a knife that is supported in a guided manner in a longitudinal direction. The knife can be moved in longitudinal direction by means of an operation element. The operation element is movably coupled with the knife by means of a coupling device, wherein the coupling device comprises a telescopic lever in order to keep the space small that is required for the pivot movement during pivoting of the operation element around a pivot axis. During pivoting of the operation element from an initial position in a working position the telescopic lever retracts upon contact with a housing wall and is subsequently extended again. In doing so, it is allowed to keep the housing small. In addition, a not illustrated bias element is provided that is supported on one side on the telescopic lever and on the other side on the operation element in order to bias the operation element in its initial position.

The arrangements known to date are elaborate in terms of construction, which results in high costs, particularly for single-use instruments. In reusable instruments the cleaning and sterilization is problematic, particularly if helical springs or telescopic arrangements are used. At this location contaminations cannot be removed or only be removed with great efforts.

SUMMARY

Thus, it can be considered as object of embodiments of the present invention to provide a surgical instrument that ensures a cheap construction and a simple cleaning.

This object may be solved by a surgical instrument having the features of claim 1.

Embodiments of the inventive surgical instrument comprise a tool, e.g. a knife, that is movably arranged in a longitudinal direction. For operating the tool, an operation element is provided. The operation element is pivotably supported. It can be pivoted between an initial position and a working position.

A movement coupling between the operation element and the tool is established via a coupling device. The coupling device comprises a coupling link. A coupling link is configured to transfer the pivot movement of the operation element on the tool and/or on a part that is particularly immovably connected with the tool. In a preferred embodiment the coupling link forms a connecting rod of the coupling device. The connecting rod that is preferably formed by the coupling link is supported at one end to execute a rotating or pivoting movement and at the other end in order to carry out a substantially straight movement in longitudinal direction.

The coupling link is elastically deformable. In the initial position of the operation element the coupling link is not elastically deformed or less elastically deformed than in the working position of the operation element and assumes a first condition. In the working position of the operation element the coupling link is more deformed as in its first condition and thus effectuates a resetting torque on the pivotably supported operation element in direction toward the initial position. The condition of the elastically deformed coupling link in the working position of the operation element is denoted as second condition.

Thus, according to embodiments of the invention, the coupling link itself effectuates the resetting torque on the operation element in order to move it back in the initial position. Additional elements for creating the resetting torque, and particularly helical springs, can be omitted.

It is advantageous, if the coupling device and for example the coupling link is releasably connected with the tool. This releasable connection can be particularly force-fit and/or form-fit and for example realized by a latch connection. In doing so, the tool can be replaced and the coupling device or the coupling link can remain in the instrument. Alternatively or additionally, such a releasable connection can also be provided at another location of the coupling device, e.g. at the connection between the coupling device and the operation element.

In an embodiment the releasable connection can be realized by a groove in the tool in which the coupling device or the coupling link engages. At least a force-fit connection is achieved due to an elastic deformation force in the first condition of the coupling link.

Preferably the tool is in a retracted position in the initial position of the operation element. In the working position of the operation element the tool can take an extended position. In a retracted position the tool is without effect on the biological tissue. In an extended position the tool can act upon the biological tissue.

Preferably the surgical instrument can comprise two jaws that are pivotably supported at each other. The tool is movably supported in one of the jaws, e.g. in a tool channel. The tool can be a knife, whereby the tool channel forms a knife channel. For example, a knife can cut biological tissue in the extended position.

Preferably the coupling link, e.g. the connecting rod, connects two parts that are arranged with distance to each other. These parts can be formed by the operation element or a part that is movably connected therewith on one hand on from the tool or a connection part that is movably connected therewith on the other hand. Without the coupling link a movement transmission from the operation element on the tool would not be possible.

The coupling link is particularly integrally formed in one piece. It is made from an elastically deformable material, e.g. from a metallic material, particularly a metallic alloy. As an option, it can be provided with a protective layer to protect the coupling link against chemical influences, whereby the protective layer has no relevance for the movement coupling.

In a preferred embodiment the coupling link is attached with one end directly at the operation element with distance to the pivot axis of the operation element. The respective other end of the coupling link can be directly arranged on the tool or on a connection part that is movably coupled therewith. Particularly the connection part is immovably arranged on the tool. The coupling link can be configured to transfer a pivot movement of the operation element in a linear movement of the tool. The coupling link can be the sole part that is provided for the transmission of the pivot movement in the linear movement.

It is advantageous, if the coupling link has a bracket-shaped form. For example, it can be configured as wire bracket or stamped bracket. Particularly, the coupling link can comprise at least one longitudinal leg and an adjoining transverse leg. The transverse leg extends particularly orthogonal to the movement direction of the tool that is orthogonal to the longitudinal direction. The at least one longitudinal leg extends preferably inclined to the longitudinal direction with an angle that has an amount between 0 degrees and 90 degrees, preferably between 10 degrees and 80 degrees and further preferably between 20 degrees and 70 degrees.

It is particularly advantageous, if the coupling link comprises two and particularly exactly two longitudinal legs that are connected with each other via the transverse leg. Preferably the transverse leg forms an end of the coupling link and particularly the end that is assigned to the tool.

Each longitudinal leg can have a free leg end that is preferably not directly connected with each other and further preferably not in direct contact with each other. Particularly the free leg ends of the longitudinal legs are arranged offset to one another with reference to a plane that is orientated orthogonal to the transverse direction. Particularly the free leg ends are arranged along a common straight line in extension direction of the longitudinal legs within this plane, if the coupling link is in its non-deformed rest condition that can, e.g. correspond to the first condition.

The longitudinal legs of the coupling link can have different lengths.

It is preferred that the longitudinal legs and the transverse leg extend in a common plane in the initial position of the operation element. Outside of the initial position and particularly in the working position of the operation element the longitudinal legs can include an angle that is larger than zero. The included angle between the longitudinal legs is largest in the working position and decreases toward the initial position, whereby it is preferably equal to zero in the initial position.

It is particularly advantageous, if the longitudinal legs are elastically non-deformed in the second condition of the coupling link (working position of the operation element) compared with the first condition of the coupling link (initial position of the operation element). For example, if the longitudinal legs extend in a straight line in the first condition of the coupling link, they preferably also extend substantially along a straight line in the second condition of the coupling link. The longitudinal legs can thus be particularly bending resistant against a bending transverse to their extension direction. In this configuration a force applied in longitudinal direction on the tool from outside can be supported via the coupling link on the operation element very well. The tool is thus not urged back out of its extended position to the retracted position in an undesired manner. This support effect is particularly improved, if the longitudinal legs include an angle larger than zero in the working position. The angle between the longitudinal legs is measured in a projection plane that is orientated orthogonal to the transverse direction and thus orthogonal to the transverse leg.

In case the longitudinal legs extend curved and/or angled and/or bent in the first condition of the coupling link, this shape can be maintained in the second condition of the coupling link.

Independent from the number of longitudinal legs, the transverse leg is preferably twisted around its extension direction in the second condition of the coupling link (working position of the operation element). This torsion creates a torque on the at least one longitudinal leg connected with the transverse leg, whereby a resetting torque is created.

It is advantageous, if the coupling link extends along a straight line or at least less bent between its two ends in the first condition than in the second condition. At least in the second condition the coupling link can extend in a curved manner between its two ends. In this embodiment the coupling link can have a bracket-shaped form or can be configured in the type of a leaf spring as two-dimensional element. In this embodiment the coupling link can be attached at one end or at both ends in a torque-proof manner, particularly at one end connected in a torque-proof manner with the operation element and/or at the other end connected in a torque-proof manner with the tool or a connection part that is immovably connected with the tool.

In an embodiment the coupling link that is at least elastically deformed outside its first condition can apply a force or force component on the tool or a connection part connected with the tool orthogonal to the longitudinal direction and particularly also orthogonal to the transverse direction. In this manner it is, for example, possible to latch the tool or the connection part in at least one predefined position in longitudinal direction.

BRIEF DESCRIPTION OF THE DRAWINGS

Preferred embodiments of the inventive surgical instruments are derived from the dependent claims, the description and the drawings. In the following, preferred embodiments are explained in detail with reference to the attached drawings. The figures of the drawings show:

DETAILED DESCRIPTION

Figure 1:
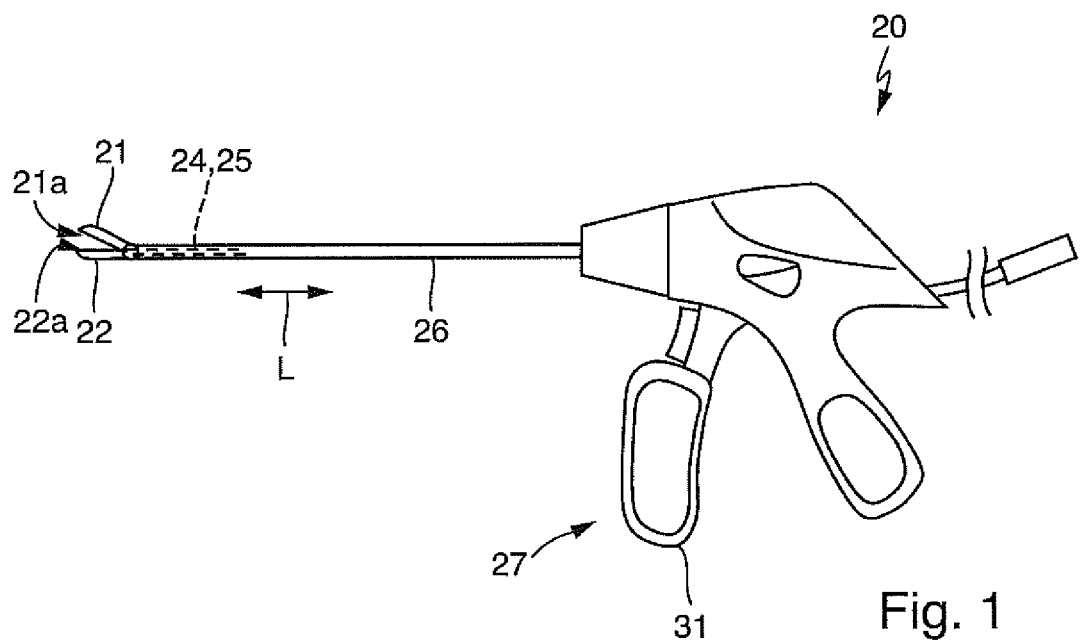
FIGS. 1 and 2 show a schematic side view of a surgical instrument, particularly an electrosurgical instrument respectively.
Figure 2:
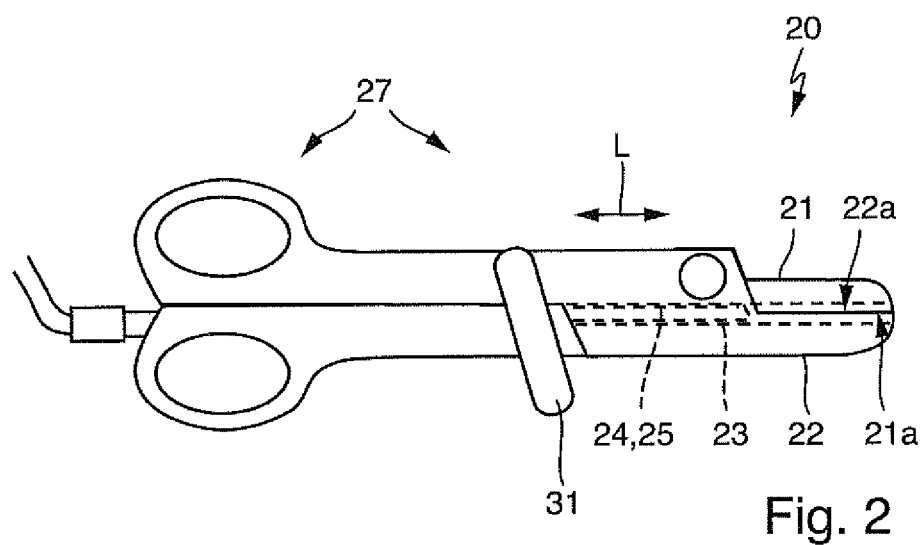

Different embodiments of a surgical instrument 20 are illustrated schematically in FIGS. 1 and 2. As illustrated, the surgical instrument 20 can be configured as electrosurgical instrument. It can be a monopolar or bipolar electrosurgical instrument. The surgical instrument is particularly a reusable instrument. It has to be cleaned and sterilized after each use.

In the illustrated embodiments the surgical instrument 20 has two jaws 21, 22 that are pivotably supported at one another. Each jaw 21, 22 has a tissue contact surface 21a or 22a. The jaws 21, 22 can be pivoted toward or away from each other to clamp or release a biological tissue between the tissue contact surfaces 21a, 22a.

The surgical instrument 20 further comprises a tool 24. The tool 24 is movably supported in longitudinal direction L in a tool channel 23. For example, the tool 24 can be formed by a knife 25. The tool channel 23 can extend in a shank 26 adjoining the jaws 21, 22 (FIG. 1) and/or can extend in one of the jaws 21, 22 (FIG. 2).

The instrument 20 comprises a handling unit 27. By means of the handling unit 27 the jaws 21, 22 can be pivoted relative to each other and the tool 24 can be moved in longitudinal direction L. In electrosurgical instruments an electric voltage can be applied to the tissue contact surfaces 21a, 22a by means of the handling unit 27.

The tool 24 and according to the example, the knife 25 can be moved in longitudinal direction L between a retracted position E and an extended position A. For this the instrument 20 comprises an operation device 30. Different embodiments of the operation device 30 or components thereof are schematically illustrated in FIGS. 3-17.

The operation device 30 comprises an operation element 31 that is part of the handling unit 27 for operating the instrument 20. The operation element 31 can be configured as separate operation element of the handling unit 27 (FIG. 2) or can alternatively be formed by an operation element that also comprises one or more additional functions (FIG. 1).

The operation element 31 is pivotably supported around a pivot axis. In the embodiment the pivot axis extends in a transverse direction Q that is orientated orthogonal to the longitudinal direction L. The pivot axis is defined by a pivot joint 32 by means of which the operation element 31 is pivotably supported on a stationary or with regard to the housing of the instrument 20 immovably arranged part. The operation element 31 has two arms 33, 34 that extend originating from the pivot joint 32. The arms 33, 34 can extend in different and particularly opposite directions, as illustrated in the embodiment.

A first arm 33 serves for manual operation. A second arm 34 is movably coupled with the tool 24 via a coupling device 35.

The coupling device 35 comprises an elastically deformable coupling link 36. In the embodiment the coupling device 35 is formed by the coupling link 36. Additional parts for movement transmission can be omitted. According to the example, the coupling link 36 is arranged with a first end 37 on the operation element 31 and particularly the second arm 34. From the first end 37 the coupling link 36 extends to a second end 38 that is assigned to the tool 24 or a connection part 39 that is preferably immovably connected with the tool 24. In the embodiments illustrated here the second end 38 is arranged on the connection part 39. In modification thereto it could also be directly arranged on the tool 24.

Due to the movement coupling between the tool 24 and the operation element 31 by means of the coupling device 35, the pivot movement of the operation element 31 around the pivot axis or the pivot joint 32 can be transmitted in a movement of the tool 24 in longitudinal direction L, particularly in order to move the tool 24 between the retracted position E and the extended position A. If the tool 24 is in the retracted position E, the operation element 31 is in a initial position I (FIGS. 3, 6, 9, 12, 16). If the tool 24 is in the extended position A, the operation element 31 is in a working position W (FIGS. 4, 7, 13, 17).

In order to pivot the operation element 31 out of the initial position I in the working position W, an operator can apply an operating force FB on the first arm 33.

Figure 16:
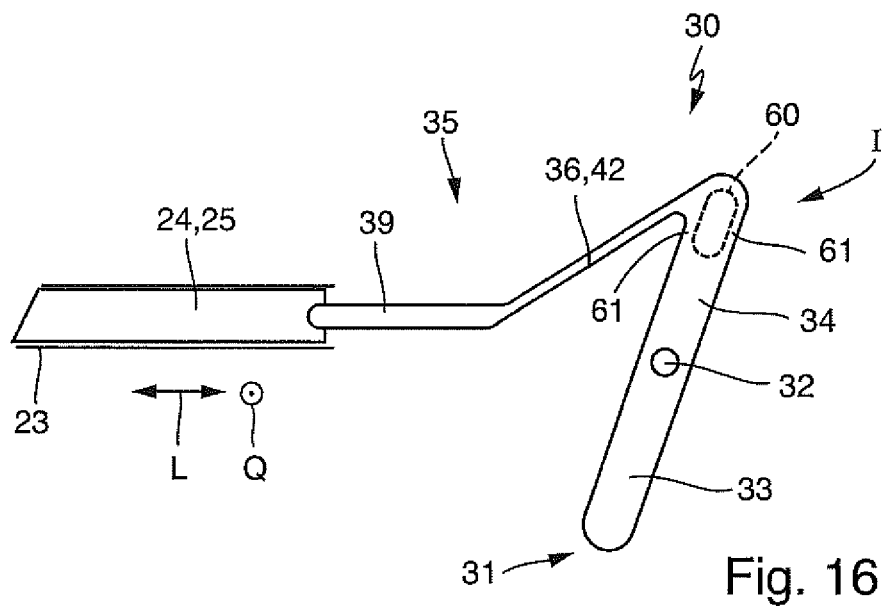
FIG. 16 shows a further embodiment of an operation device for the surgical instrument in a schematic side view, wherein an operation element of the operation device is in an initial position and a coupling link of a coupling device is in a first condition
Figure 17:
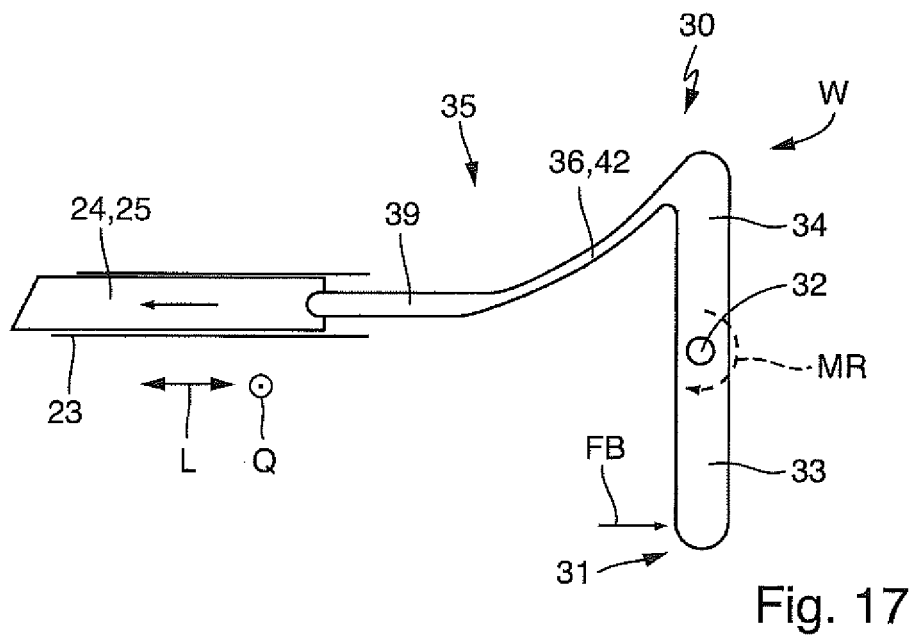
FIG. 17 shows the embodiment of the operation device of FIG. 16 and a schematic side view, wherein the operation element is in a working position and the coupling link of a coupling device is in a second condition.

According to embodiments of the invention, the coupling link 36 is configured in an elastically deformable manner. In the preferred embodiments described here the coupling link 36 is integrally formed and thus does not comprise seams or joints. It can form a separate part from the operation element 31 (FIGS. 3-15) or can alternatively be integrally formed with the operation element 31. In addition or as an alternative, the coupling link 36 can be integrally formed with the connection part 39 (FIGS. 16 and 17). In modification to the embodiment illustrated in FIGS. 16 and 17, the coupling link 36 can also be integrally formed either only with the operation element 31 or only with the connection part 39 and apart therefrom arranged or attached as illustrated or explained with regard to the other embodiments.

In the preferred embodiments described here the coupling link 36 forms a connecting rod 42. The connecting rod 42 is configured to transmit the pivot movement of the second arm 34 in a linear movement in longitudinal direction L of the tool 24 or the connection part 39. According to the example, the first end 37 is thus arranged on the second arm 34 and thus pivotably supported around the pivot axis S or the pivot joint 32. The first end 37 of the coupling link 36 is arranged with distance to the pivot axis or the pivot joint 32. The second end 38 of the coupling link 36 is shiftably arranged in longitudinal direction L together with the tool 24 or the connection part 39. Thus, the coupling link 36 can also be denoted as connecting rod 42.

Figure 3:
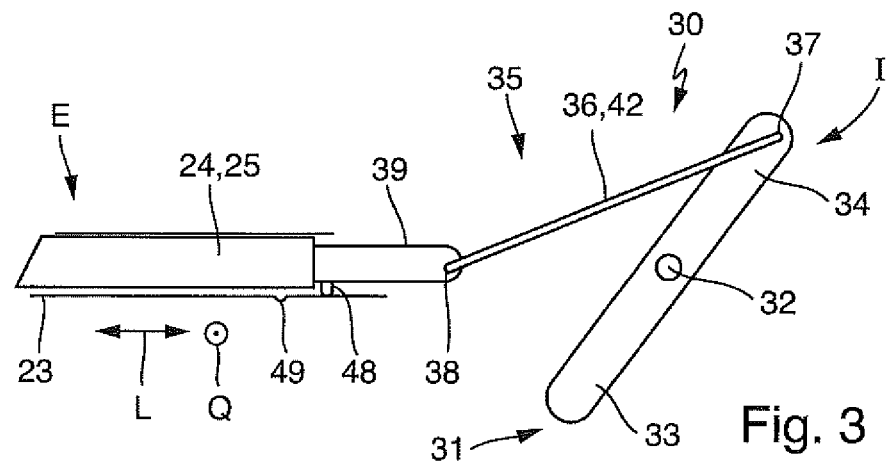
FIG. 3 shows an embodiment of an operation device of the surgical instrument in a schematic side view, wherein the operation element of the operation device is in an initial position and the coupling link of a coupling device is in a first condition.
Figure 4:
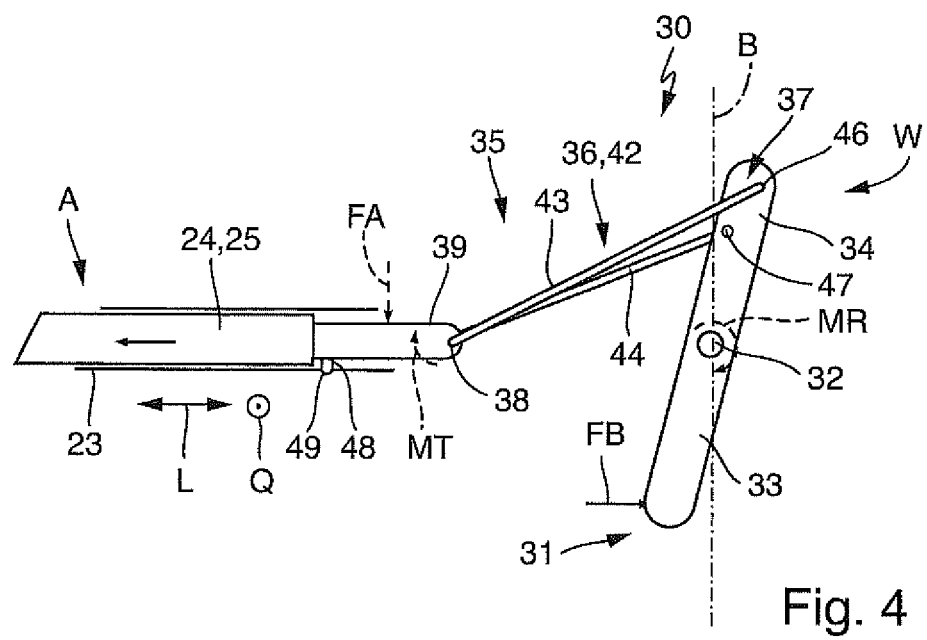
FIG. 4 shows the operation device of FIG. 3 in a schematic side view, wherein the operation element is in a working position and a coupling link of a coupling device is in a second condition.
Figure 5:
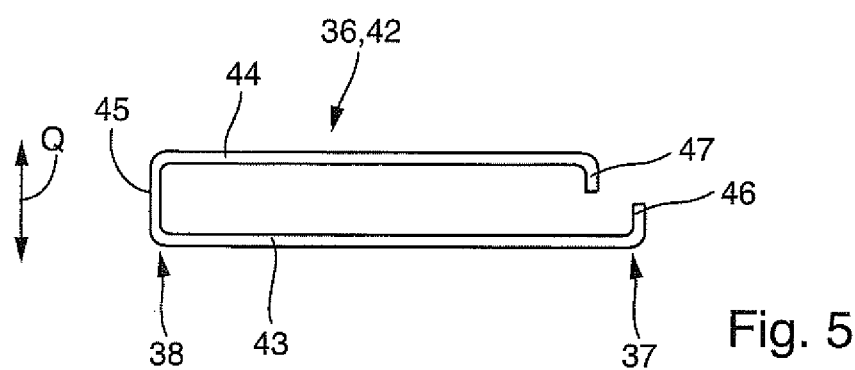
FIG. 5 shows an embodiment of a coupling link of the operation device of FIGS. 3 and 4 in a top view.

In the embodiment of the operation device 30 illustrated in FIGS. 3-5 the coupling link 36 comprises a first longitudinal leg 43 and a second longitudinal leg 44. The two longitudinal legs 43, 44 are arranged with distance in transverse direction Q relative to each other. On the second end 38 the two longitudinal legs 43, 44 are connected with each other by a transverse leg 45 extending in transverse direction Q and are, according to the example, integrally formed.

On the second end 37 the first longitudinal leg 43 comprises a first free leg end 46 and the second longitudinal leg 44 comprises a second free leg end 47. The free leg ends 46, 47 are bent or angled relative to the longitudinal legs 43, 44 and extend, according to the embodiment, substantially parallel to the transverse leg 45, i.e. in transverse direction Q. The first free leg end 46 and the second free leg end 47 are, according to the example, shorter than the transverse leg 45.

As particularly apparent from FIGS. 4 and 5, the free leg ends 46, 47 are arranged offset or with distance to each other in a projection plane that is orientated orthogonal to the transverse direction Q. In the embodiment this is achieved in that the first longitudinal leg 43 has a longer length from the transverse leg 45 to the first free leg end 46 than the second longitudinal leg 44 from the transverse leg 45 to the second free leg end 47.

The transverse leg 45 can extend in transverse direction Q through a through-hole extending through the connection part 39. Alternatively, the transverse leg 45 can also engage or can be latched in a groove on the connection part 39 and/or on the tool 24 that is open toward the top such that a releasable connection is established between the tool 24 and the coupling device 35. This can facilitate the assembly and/or replacement of the tool independent from the coupling device 35.

The two free leg ends 46, 47 can extend into a holding hole in the second arm 34. According to the example, the coupling link 36 is supported rotatably or in a hinged manner on the connection part 39 as well as on the second arm 34.

In the initial position I of the operation element 31 the coupling link 36 is in a first condition. In the first condition the coupling link can be elastically undeformed. In the working position W of the operation element 31 the coupling link 36 is in a second condition being elastically deformed compared with the first condition.

In the first condition of the coupling link 36 the two longitudinal legs 43, 44 and the transverse leg 45 extend in a common plane (FIG. 3). If the operation element 31 is pivoted out of its initial position I, the two longitudinal legs 43, 44 are inclined relative to each other with view in a projection plane that is orientated orthogonal to the transverse direction Q. This can be traced to the fact that the support locations of the two free leg ends 46, 47 outside the initial position I are no longer located in a common plane together with the transverse leg 45. The inclination of the two longitudinal legs 43, 44 relative to one another outside of the initial position I results in that the transverse leg 45 is twisted and thus a twisting torque MT in circumferential direction around the transverse leg 45 is created that urges the too longitudinal legs 43, 44 to take the position in the common plane with the transverse leg 45. In doing so, concurrently a resetting torque MR is applied on the operation element 31 that urges the operation element 31 back into its initial position I.

According to the example, in the working position W of the operation element 31 the two free leg ends 46, 47 are arranged on the same side relative to a reference plane B that extends orthogonal to the longitudinal direction L along the pivot axis of the operation element 31 (FIG. 4). Particularly, the two free leg ends 46, 47 are arranged on the one side and the second end 38 of the coupling link 36 is arranged on the other side of the reference plane B in the working position W of the operation element 31.

Thus, the coupling link 36 does not only form a mechanical element by means of which the movement coupling between the operation element 31 and the tool 24 is established, but concurrently also a resetting device, whereby the operation element 31 is urged back in its initial position I. Without application of an operating force FB on the operation element 31 it takes the initial position I and the tool 24, according to the example the knife 25, is pulled back in the retracted position E. Additional elastically deformable resetting components, particularly helical springs, can be omitted. In doing so, the construction of the coupling device 35 is very simple. The number of required components in the coupling device 35 or the operation device 30 is reduced. The simple construction also facilitates the cleaning. Particularly by avoiding helical springs in which the windings can tightly abut against each other, the cleaning or sterilization is remarkably simplified.

A further optional configuration possibility of the operation device 30 is highly schematically illustrated in FIGS. 3 and 4. According to the example, the coupling link 36 creates a force component in a direction orthogonal to the longitudinal direction L and orthogonal to the transverse direction Q that is denoted as pressing force FA. This force component is created, if in the embodiment according to FIGS. 3 and 4 the transverse leg 45 is twisted, i.e. at least outside of the initial position I. The pressing force FA can be used in order to press a latch projection 48 on the tool 24 and/or on the connection part 39 in an assigned latch recess 49 adjacent to the tool channel 23. It is also possible that multiple latch projections 48 and/or multiple latch recesses 49 are provided. In doing so, the tool 24 can be latched during the movement in longitudinal direction L in at least one position. A feedback about the actually achieved position of the tool 24 relative to the tool channel 23 or relative to the jaws 21, 22 can be provided to an operator, due to the latching. In FIG. 4 the latching is illustrated in the extended position A of the tool 24, wherein the latched position can also be predefined in at least one other arbitrarily defined position of the tool 24 relative to the tool channel 23.

Figure 6:
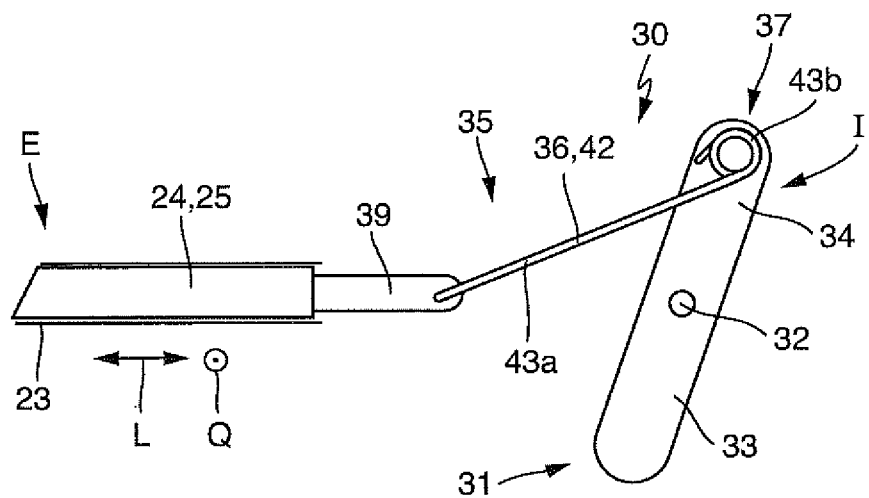
FIG. 6 shows a further embodiment of an operation device for the surgical instrument in a schematic side view, wherein the operation element of the operation device is in an initial position and the coupling link of a coupling device is in a first condition.
Figure 7:
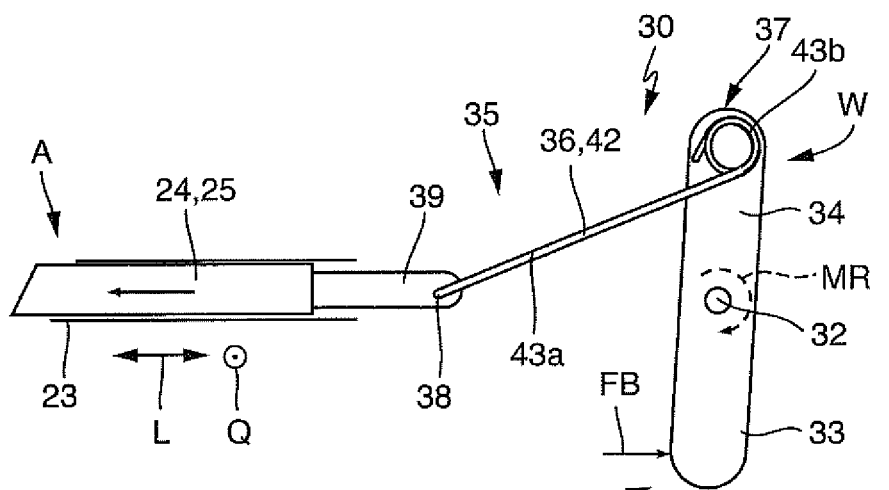
FIG. 7 shows the embodiment of the operation device of FIG. 6 in a schematic side view, wherein the operation element is in a working position and the coupling link of the coupling device is in a second condition.
Figure 8:
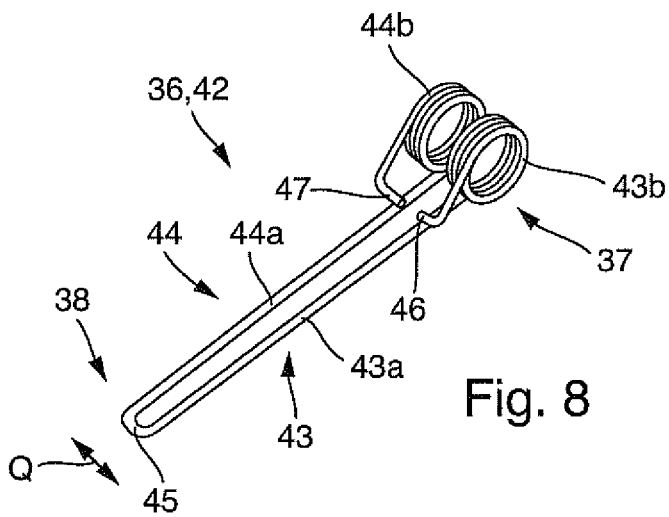
FIG. 8 shows a perspective illustration of an embodiment of a coupling link of the operation device according to FIGS. 6 and 7.

In FIGS. 6-8 a further embodiment of the operation device 30 or the coupling link 36 is illustrated. Apart from the embodiment of the coupling link 36, this embodiment of the operation device 30 can correspond to the embodiment described based on FIGS. 3-5 above. Thus, reference is made to the above description.

The modified coupling link 36 is particularly apparent from FIG. 8. Analog to the embodiment according to FIG. 5, the coupling link 36 comprises a bracket-shaped form having a first longitudinal leg 43, a second longitudinal leg 44 and a transverse leg 45 at the second end 38. The opposite first end 37 of the coupling link 36 is configured differently than in the embodiment according to FIG. 5. Both longitudinal legs 43, 44 have preferably the same length and the free leg ends 46, 47 extending in transverse direction Q are preferably aligned along a common straight line in transverse direction Q. Each longitudinal leg 43, 44 has a leg section 43a, 44a extending along a straight line originating from the transverse leg 45 and a curved leg section 43b, 44b directly adjoining the straight leg section 43a, 44a. In a rest condition that is not subject to a force, the curved leg section 43b, 44b comprises an arc-shaped and particularly a circular arc-shaped extension. In the embodiment illustrated in FIG. 8, the curved leg section 43b, 44b comprises at least one complete winding and according to the example multiple windings. The wound or curved leg section 43b, 44b establishes a connection between the respective straight leg section 43a, 44a and the respective leg end 46, 47. According to FIG. 8, the coupling link 36 is integrally formed and can be, for example made by bending a wire. As apparent from FIG. 8, the free leg ends 46, 47 are arranged closer to the transverse leg 45 than the wound or curved leg sections 43b, 44b.

Analog to the embodiment according to FIGS. 3-5, the transverse leg 45 extends through a through-hole in the connection part 39 or alternatively in the tool 24. The free leg ends 46, 47 respectively engage a recess or depression on the second arm 34.

If now the operation element is moved out of the initial position I by application of an operating force FB, the tension in the respective wound or curved leg section 43b, 44b is changed and the coupling link 36 tends to take the condition that it has in the initial position I. In this manner a resetting torque MR around the pivot axis or the pivot joint 32 is created.

In the embodiment according to FIGS. 3-5 as well as in the embodiment according to FIGS. 6-8, the longitudinal legs 43, 44 or the straight leg sections 43a, 44a are bending-resistant against a bending transverse to their extension direction. In doing so, a force applied externally on the tool 24 is very well supported via the coupling link 36 on the operation element 31.

Figure 9:
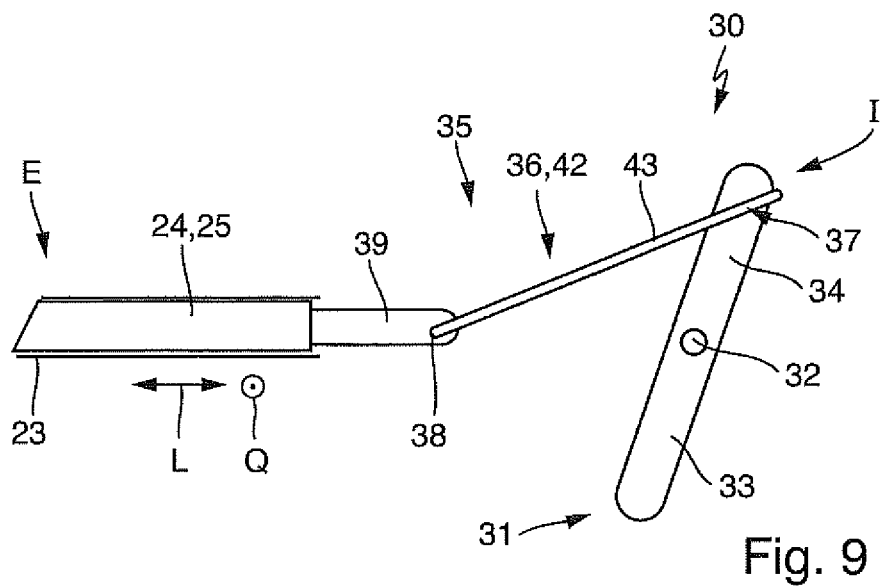
FIG. 9 shows a further embodiment of the operation device for the surgical instrument in a schematic side view, wherein an operation element of the operation device is in an initial position and a coupling link of a coupling device is in a first condition.
Figure 10:
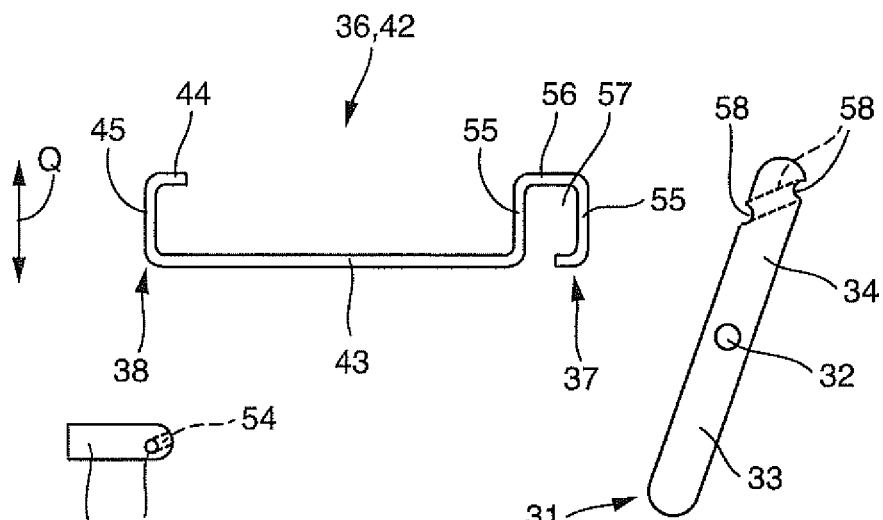
FIG. 10 shows the operation element, a coupling link and a connection part of the operation device of FIG. 9 in a schematic individual illustration.
Figure 11:
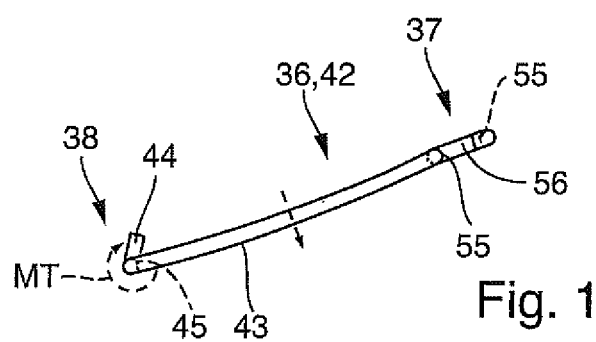
FIG. 11 shows the coupling link of the operation device according to FIGS. 9 and 10 in a schematic side view, wherein the coupling link is elastically deformed and is in its second condition.

Another embodiment of the operation device 30 is apparent from FIGS. 9-11 that is similar to the embodiment according to FIGS. 3-5 such that reference can be made to the description of these figures. The substantial difference in this embodiment is that only one longitudinal leg 43 is provided that connects the transverse leg 45 on the second end 38 with the first end 37. The second longitudinal leg 44 only extends originating from the transverse leg 45 in an area of the second end 38 and serves there to arrange the coupling link 36 on the tool 24 and according to the example on the connection part 39 in a torque-proof manner relative to the transverse leg 45. For this the short second longitudinal leg 44 can be arranged in a groove 54 adjoining a through-hole 53 for the transverse leg 45, as an example. The transverse leg 45 remains twistable around an extension direction, if the first longitudinal leg 43 is moved or pivoted relative to the second longitudinal leg 44 that is arranged in a torque-proof manner, due to the operation of the operation element 31.

The first end 37 of the coupling link 36 is fixed on the operation element 31. For example, the coupling link 36 can be bent multiple times on the first end 37 such that two holding legs 55 are formed that extend in transverse direction Q and that are connected by means of a connecting leg 56. In the area between the two holding legs 55 an interstice 57 is limited in which the second arm 34 may extend. The holding legs 55 and the connecting leg 56 embrace the second arm 34 of the operation element 31 so to speak. For the attachment a holding groove 58 can be provided in the second arm 34 in which at least the holding legs 55 and/or the connecting leg 56 is/are arranged.

In FIG. 11 the force and torque application of the coupling link 36 is highly schematically illustrated, if the operation element 31 is deflected from its initial position I. Due to the pivot movement of the two longitudinal legs 43, 44 relative to each other around the transverse leg 45, a twisting torque MT is created at the transverse leg 45. In addition, the first longitudinal leg 43 can be bent out of its straight extension. Due to these forces and torques, a resetting torque MR is created around the pivot axis S or the pivot joint 32 that urges the operation element 31 back in its initial position I.

Figure 12:
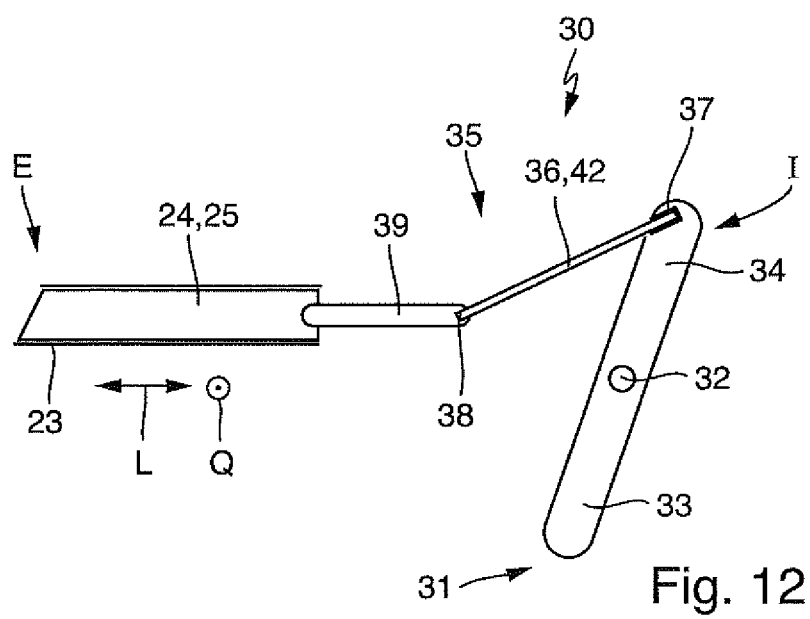
FIG. 12 shows a further embodiment of an operation device for the surgical instrument in a schematic side view, wherein the operation element of the operation device is in an initial position and a coupling link of a coupling device is in a first condition.
Figure 13:
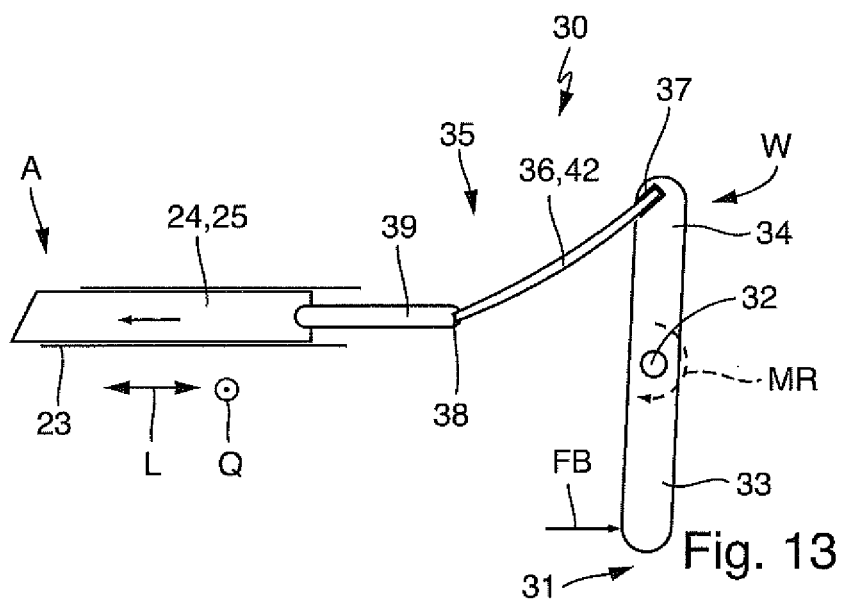
FIG. 13 shows the embodiment of the operation device of FIG. 12 in a schematic side view, wherein the operation element is in a working position and a coupling link of a coupling device is in a second condition.

In the embodiment of the operation device 30 illustrated in FIGS. 12 and 13 the configuration corresponds to the embodiments described above apart from the configuration of the coupling link 36. The coupling link 36 is configured in this embodiment such that it is bent out of its initial extension in the initial position I of the operation element 31 and thereby creates the resetting torque MR.

Figure 14:
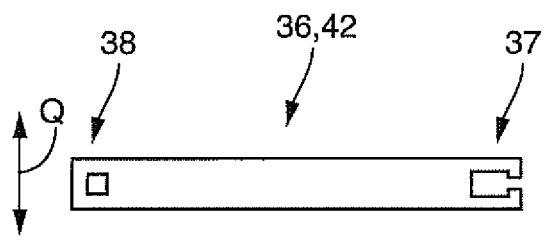
FIGS. 14 and 15 show a schematic basic illustration of a coupling link of the operation device according to FIGS. 12 and 13 in a top view respectively.
Figure 15:
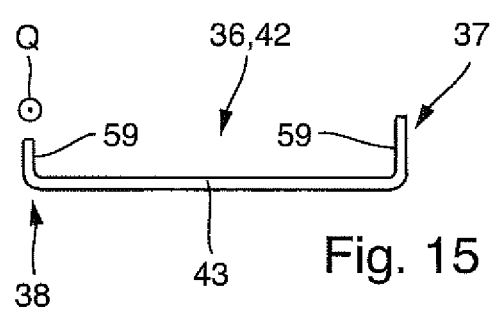

In FIGS. 14 and 15 embodiments for the coupling link 36 are illustrated. The coupling link 36 can have a form of a leaf spring, as schematically illustrated in FIG. 14. The coupling link 36 is attached at the first end 37 on the second arm 34 and at the second end 38 on the tool 24 or on the connection part 39 in an orientation that it takes in the initial position I. In doing so, a bending of the coupling link 36 is created during pivot movement of the operation element 31. The coupling link 36 tends to take its initial position and in this manner creates the resetting torque MR.

For attachment of the coupling link 36 it can have at least one through-opening and/or at least one recess that is open in an outward direction at the first end 37 or at the second end 38. The portions limiting the recess can be arranged in grooves or recesses, e.g. on the second arm 34. By means of the through-opening the coupling link 36 can be overmolded with the material of the connection part 39 at the second end 38, for example. The connection at the first end 37 and at the second end 38 can be form-fit and/or force-fit and/or a substance bond and/or an adhesive bond. Overmolding of the coupling link 36 is preferably possible on one of the two ends 37 or 38 or alternatively also on both ends 37 and 38.

Instead of a leaf-spring-like coupling link 36, as illustrated in FIG. 14, the coupling link 36 can also be formed by a wire element or wire bracket (FIG. 15). It consists particularly of a longitudinal leg 43 that extends between the first end 37 and the second end 38 and that transitions at the first end 37 as well as at the second end 38 in an end leg 59 extending orthogonal to the longitudinal leg 43. The two end legs 59 extend preferably parallel to one another and particularly in a plane that is orientated orthogonal to the transverse direction. The two end legs 59 can be inserted in respective holes or recesses on the second arm 34 or on the tool 24 or the connection part 39 respectively and can be attached there as necessary, e.g. by means of an adhesive bond. During deflection of the operation element 31 out of its initial position I the longitudinal leg 43 is bent out of its initial extension, because the end legs 59 at the two ends 37, 38 are held in place in their orientation relative to the second arm 34 on one side and relative to the tool 24 or the connection part 39 on the other side.

A further embodiment of the operation device 30 is illustrated in FIGS. 16 and 17. While the coupling link 36 is a separate component in the embodiments described above, the coupling link 36 is formed integrally with the operation element 31 and/or with the connection part 39 in the embodiments according to FIGS. 16 and 17. In the illustrated embodiment the operation element 31, the coupling link 36 and the connection part 39 are one single integral component that consists of plastic, for example, and can be particularly formed as injection mold part. If the coupling link 36 is integrally formed only with the operation element 31 or only with the connection part 39, it can be connected at the respective other end 37 or 38 in a force-fit manner and/or form-fit manner and/or by substance bond and/or by adhesive bond with the operation element 31 or the connection part 39 respectively.

Analog to the embodiments according to FIGS. 12-15, the coupling link 36 forms a bending spring and can thus have the form of a leaf spring similar to the embodiment according to FIG. 14 or a web-shaped form similar to the straight longitudinal leg 43 according to FIG. 15. The function corresponds to the embodiment according to FIG. 12 or 13.

FIG. 16 also shows a further optional possibility. In addition to effectuating the resetting torque MR by a deformation of the coupling link 36, the resetting torque MR can also be at least partly created by a deformation of the second arm 34 of the operation element 31. In order to allow this deformation, the second arm 34 can have a respective deformable configuration. In FIG. 16 this is by way of example illustrated by through-opening 60 that extends through the second arm. Adjacent to the through-opening 60 the second arm 34 comprises web-shaped sections 61 that are sufficiently small dimensioned in cross-section. In doing so, a bending or deforming of the web-shaped sections 61 and/or a movement of the web-shaped sections toward each other is allowed. If this area of the second arm 34 is deformed (outside of the initial position I), the second arm 34 tends to take its undeformed initial shape and thus creates at least a component of the resetting torque MR.

In another modification of the operation device 30 it would be possible to configure the coupling link 36 undeformably stiff with regard to the applied forces and to only configure at least a part of the second arm 34 in a deformable manner in order to create the resetting torque MR.

In all of the bracket-shaped configurations of the coupling link, particularly in the embodiments according to FIGS. 3-11 and 15, the coupling link 36 can be formed by a wire bent part. The wire can have a circular cross-section. Preferably the wire consists of a metallic alloy.

The deformability of at least a part of the second arm 34 and/or the latch means 48, 49 explained in connection with FIGS. 3 and 4 can be provided in all of the embodiments.

In all of the embodiments a releasable connection between the tool 24 and the coupling device 35 can be provided indirectly via the connection part 39 or also directly, e.g. a force-fit and/or form-fit connection, preferably a latch connection.

Embodiments of the invention include an operation device 30 for operating a tool 24 of a surgical instrument 20. The operation device 30 has an operation element 31 that is pivotably supported between an initial position I and a working position W. The operation element 31 is movably coupled with the tool 24 by means of a coupling device 35 comprising a coupling link 36 or consisting of a coupling link 36. The coupling link 36 is elastically deformable and effectuates a resetting torque MR due to the elastic deformation in case the operation element 31 is deflected out of the initial position I, wherein the resetting torque MR urges the operation element 31 back in the initial position I. Additional spring elastic resetting elements can thus be omitted.

The invention claimed is:

1. A surgical instrument for treating tissue comprising:
a coupling link comprising;
    a first end and a second end, wherein the first end and the second end are on opposite ends of the coupling link, and
    a first longitudinal leg and a transverse leg adjoining thereto that extends in a transverse direction orthogonal to a longitudinal direction;
a tool coupled to the first end of the coupling link and is movably supported in the longitudinal direction in a guided manner; and
an operation element coupled to the second end of the coupling link such that the operation element is pivotably supported to be pivoted between an initial position and a working position relative to the coupling link;
wherein the transverse leg is twisted around its extension direction in the working position of the operation element;
wherein the coupling link establishes a movement between the operation element and the tool, wherein the coupling link is elastically deformable and is elastically deformed in the working position of the operation element such that it effectuates a resetting torque in a direction toward the initial position onto the operation element.

2. The surgical instrument according to claim 1, wherein the coupling link comprises a second longitudinal leg arranged with distance to the first longitudinal leg and the first longitudinal leg and the second longitudinal leg are connected with each other via the transverse leg.

3. The surgical instrument according to claim 2, wherein the first longitudinal leg comprises a first free leg end and the second longitudinal leg comprises a second free leg end, wherein the first free leg end and the second free leg end are arranged offset with regard to each other.

4. The surgical instrument according to claim 2, wherein the two the first longitudinal leg and the second longitudinal leg have different lengths.

5. The surgical instrument according to claim 2, wherein the first longitudinal leg and the second longitudinal leg and the transverse leg are arranged in a common plane in the initial position of the operation element.

6. The surgical instrument according to claim 2, wherein the first longitudinal leg and the second longitudinal leg include an angle between the first longitudinal leg and the second longitudinal leg different to zero in the working position of the operation element when viewed from the transverse direction.

7. The surgical instrument according to claim 2, wherein at least one of the first longitudinal leg and the second longitudinal leg is elastically undeformed in the working position of the operation element compared with the initial position.

8. The surgical instrument according to claim 1, wherein the coupling link extends along a straight line between the first end and the second end in the initial position of the operation element.

9. The surgical instrument according to claim 1, wherein the coupling link extends in a curved manner between the first end and the second end in the working position of the operation element.

10. The surgical instrument according to claim 1, wherein in the working position of the operation element, the elastically deformed coupling link applies a force on at least one of the tool and a connection part connected with the tool in a direction orthogonal to the longitudinal direction.

11. The surgical instrument according to claim 1, wherein the coupling link is not a helical spring.

12. The surgical instrument according to claim 1, wherein the coupling link has a bracket-shaped form or is configured as a leaf spring.

* * * * *